(12) United States Patent
Pischel et al.

(10) Patent No.: US 6,503,951 B2
(45) Date of Patent: *Jan. 7, 2003

(54) USE OF CREATINE AND/OR CREATINE DERIVATIVES FOR TREATING TYPICAL DISORDERS IN WOMEN

(75) Inventors: Ivo Pischel, Trostberg (DE); Helen Louise Holland, Halifax (GB); Brigitta Schwartz, Kastl (DE); Andrea Huber, Marietta, GA (US); Ralf Jäger, Trostberg (DE)

(73) Assignee: SKW Trostberg Aktiengesellschaft, Trostberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/491,662

(22) Filed: Jan. 27, 2000

(65) Prior Publication Data

US 2002/0072541 A1 Jun. 13, 2002

(30) Foreign Application Priority Data

Jun. 30, 1999 (DE) .......................... 199 29 995

(51) Int. Cl.⁷ ............................. A61K 31/155
(52) U.S. Cl. .................................... 514/634
(58) Field of Search ......................... 514/634

(56) References Cited

U.S. PATENT DOCUMENTS

| 5,627,172 A | 5/1997 | Almada et al. ............. 514/120 |
| 6,080,788 A | 6/2000 | Sole et al. .................. 514/516 |
| 6,143,300 A | * 11/2000 | Stevenot ................. 424/195.1 |

FOREIGN PATENT DOCUMENTS

| WO | 94 17794 A | | 8/1994 |
| WO | 96 14063 A | | 3/1996 |
| WO | 96/14063 | * | 5/1996 |
| WO | 98 28263 A | | 7/1998 |
| WO | 99 00122 A | | 1/1999 |

* cited by examiner

Primary Examiner—Theodore J. Criares
Assistant Examiner—Jennifer Kim
(74) Attorney, Agent, or Firm—Fulbright & Jaworski LLP

(57) ABSTRACT

The invention relates to the use of creatine and/or creatine derivatives for treating typical disorders in women, for example PMS or dysmenorrhea, which involves the prophylactic of therapeutic use, in particular, of creatine monohydrate, creatine pyruvates, creatine ascorbates and creatine α-ketoglutarates as creatine derivatives in preferred daily doses of 0.1 g to 20 g. The invention also provides for the use of creatine or its derivatives as mixtures with a pyruvate, ascorbate or α-ketoglutarate. The creatine or its appropriate derivatives are not restricted to any particular form of application, which makes them all the more suitable for the many symptoms of typical female disorders.

8 Claims, No Drawings

USE OF CREATINE AND/OR CREATINE DERIVATIVES FOR TREATING TYPICAL DISORDERS IN WOMEN

SPECIFICATION

This invention relates to the use of creatine and/or creatine derivatives for treating typical disorders in women.

Irrespective of their age and especially in the industrialized countries, many women suffer from typical disorders which often cannot be diagnosed exactly and is therefore very difficult to treat. An added problem is that no defined causes have been identified to which these complaints can be attributed, which is why they are simply referred to as typical female ailments.

Premenstrual syndrome (PMS), for example, is characterized by physical and emotional symptoms which vary in severity from individual to individual. These symptoms appear about 7 to 10 days prior to menstruation, and disappear with its onset. Medical specialists estimate that approximately 40% of all women between the ages of 15 and 50 are affected by PMS. Typical symptoms include tenderness and swelling of the breast, abdominal fullness and digestive complaints, headaches, backache, skin disorders, hot flushes, weight increase and swollen joints. Women with PMS syndrome are tense and irritable, aggressive or melancholic, and are altogether more susceptible to existing mood swings. The causes of PMS are still largely unknown.

At present, PMS is treated in various different ways and with only moderate success. Therapies include diuretics, hormonal preparations and tranquilizers, combined with special diets.

Another typical and cyclical female ailment is dysmenorrhea, a painful form of menstruation which is not due to organic factors but to a functional or essential disturbance. Such disturbances may be due to hormonal disorders, dystonia or ideopathic causes. Dysmenorrhea, which often takes the form of painful cramps, is frequently accompanied by general symptoms such as headaches, nausea, irritability and general apathy.

Typical female ailments also include climacterial complaints, which occur both before and, in particular, after the menopause. The main climacterial complaints include vegetative and psychic disorders such as hot flushes, cold shivers, fits or perspiration and dizziness, but also palpitations and angina-pectoris-related complaints, insomnia, anxiety, decreased performance, forgetfulness, lethargy, mood swings, depression and increased irritability.

This group of disorders also includes the commonly cited menopause syndrome, or vegetative-climacterial syndrome. Of significance here is the typical combination of hot flushes, dizziness and fits of perspiration which is experienced during menopause, and which can also occur prior to menopause and, in particular, following surgical castration of young women. The menopause syndrome comprises not only neurovegetative complaints but also psychonervous disturbances such as irritability, listlessness, decreased performance, dyssomnia, etc., as well as somatic irritations in the form of atrophy of the genital organs and mammary glands, adiposity of osteoporosis.

Another typical female ailment is meteoropathy, or oversensitivity to changes in atmospheric influences such as pressure, temperature and humidity, and to special climatic situations. Treatment is designed primarily to counter lack of concentration, mood swings, general indisposition, fatigue, disturbed sleep, headaches and anxiety. There is also a special form of meteoropathy known as „föhn-wind" illness, which is manifested in the form of irritability, nausea, headaches (föhn-wind headaches), rapid fatigue and general apathy.

With many women, cyclical ailments are accompanied by migraines. Migraines are sudden, often throbbing headaches which begin in the early morning and can last for hours or even days. Migraines are often accompanied by vegetative symptoms such as nausea and vomiting, photophobia and noise sensitivity, ocular disturbances or neurologic manifestations. The reason is probably a constriction of the cranial arteries. Triggering factors can be emotional stress, climatic influences, alcoholic beverages, cigarettes etc., or medicines. All forms of migraine classified by the International headache Society (1988) are treatable, such as migraine with and without aura, migraine with typical aura, migraine with prolonged aura, familial hemiplegic migraine, basilar artery migraine, migrainous aura without headache, migraine beginning with acute aura, ophthalmoplegic migraine and retinal migraine; periodic syndromes during childhood, such as benign paroxysmal dizziness and alternating hemicrania, are also under discussion as possible precursors or attendant symptoms of a migraine, as too are migraine complications, status migrainosus, migrainous infarct and migrainous disorders which do not fulfil the above criteria.

Tension-type headaches, which are also known as idiopathic, psychogenic of muscular-contraction headaches, are a frequent form of episodic or chronic headache encountered predominantly by women and therefor also considered to be a typical female ailment. These headaches are experienced as dull bilateral headaches which extend from the back of the head to the forehead or down to the shoulders, and are accompanied by stiff head and neck musculature.

Women often express the with for a formulation which exerts a regulative effect on their sleeping-waking rhythm and leads to deeper and more relaxing sleep during the night, with no insomnia or dyssomnia (difficulty in falling asleep, disturbed sleep). Waking in the morning should then not be impaired by sleep drunkenness, and the waking rhythm should be free of lethargy and depression. Another typical female ailment is chronic fatigue disease, a controversial and sometimes endemic clinical condition characterized by a months-long decrease in physical and mental performance and an abnormally high need of sleep; there symptoms may be accompanied by headaches, muscular pain, dizziness and parasthesias. Constipation is yet another ailment known to cause problems especially in women. Last but not least, it is predominantly women who suffer from skin problems, above all acne, which is caused by various diseases of the sebaceous gland follicles. These include secretion and cornification disorders, with subsequent inflammation and scarring. Many women also suffer from woundhealing disorders.

As already described, typical disorders in women are typically of many different forms, and available treatment is still highly inadequate. This underlines the need for a broad-spectrum therapeutic agent with few side effects.

Due to the fact that selective therapy, for the reasons given, is difficult to provide, the overall object of this invention was to provide an agent for treating typical disorders in women, which is easy to absorb, shows good physiological compatibility and causes no side effects.

This object is established by the use of creatine and/or creatine derivatives. Creatine derivatives are compounds which contain creatine or creatine salts, or compounds which react to form creatine or creatine salts under physiological conditions.

Surprisingly, after treatment with creatine and/or creatine derivatives, women who suffer from typical menstrual symptoms experience a pronounced improvement in or even the complete disappearance of the known symptoms. In view of the large variety of possible disorders, this was not to be expected. The women who underwent this treatment found the marked improvement in their emotional status or frame of mind to be especially helpful.

According to this invention, creatine and hydrates thereof, especially creatine monohydrate, and physiologically compatible creatine salts of organic and inorganic acids, especially creatine pyruvates, creatine ascorbates and creatine-α-ketoglutarates, are among the agents that have been found suitable for alleviating typical disorders in women. The invention provides for a preferred daily dose of 0.1 to 20 g, and especially of 1 to 7 g.

A method of producing high-purity creatine of creatine monohydrate is disclosed in the U.S. Pat. No. 5,719,319.

High-purity creatine pyruvate, for example, is described by formula I or II, in which the crystal water content n is preferably 0 to 2. Creatine pyruvates and methods for their production are disclosed in WO 98/28263 and U.S. Ser. No. 08/893,423.

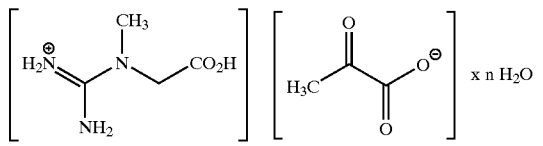

Formula I

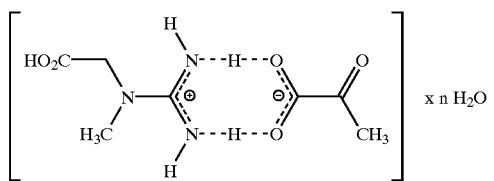

Formula II

In creatine pyruvates containing water of crystallization, the anion can also be present in the 2,2-dihydroxy form.

The creatine pyruvate of formulae I an II contains the creatine cation and the corresponding anion, or the 2,2-dihydroxypyruvate, in a molar ratio of 1:1 or approximately 1:1.

The creatine ascorbate, too, preferably contains the creatine cation and the corresponding anion in a molar ration of 1:1 or approximately 1:1. Creatine ascorbates and methods for their production are disclosed in WO 98/38183 and U.S. Pat. No. 5,863,939.

This invention also provides for the use of creatine (monohydrate) and/or creatine derivatives in mixtures with pyruvates, ascorbates and α-ketoglutarates, which need only satisfy the requirement that their respective cations exhibit good physiological compatibility. It is also of advantage to use alkaline and earth alkaline salts. Calcium pyruvates and methods for their production are disclosed in WO/99/02479 and U.S. Ser. No. 08/955,838.

The invention provides for the agent to be administered primarily as a means of therapy, but also as a prophylactic against typical disorders in women. Generally, all forms of application are possible, especially oral, topical and dermal forms. For the purpose of this invention, however, application forms such as powders, tablets and sugar-coated tablets (all especially in effervescent forms), pastilles, creams pastes and liquid formulations are especially suitable. Besides creatine and/or creatine derivatives, the formulations administered may contain additional physiologically compatible components such as carriers, eg, water, aqueous buffers and/or lipophilic carriers, absorption and penetration promoters, fillers, flavoring agents, etc, and substances which make it possible to produce forms of application with delayed release. The formulations may also contain additional pharmaceutical active agents such as Calcium and magnesium salts, St. Johns Wort, chasteberry, diuretics (eg, hydrochlorothiazides), contraceptives (eg, progesterone), progestin, GRH agonists, tranquilizers (eg, benzodiezepines) vitamins (eg, B-complex, pyridoxine), so-called serotonin-reuptake inhibitors (eg, fluxetin, sertralin) and pain killers such as prostaglandin synthetase inhibitors (iboprofen, naproxen, mefenamic acid), salicylates, acetylsalicylic acid and paracetamol.

The range of indications for typical female ailments is equally as broad as the range of forms in which the agent can be administered. For example, creatine and/or its derivatives can be used—either alone or in mixtures as provided for by the invention o for manifestations of premenstrual syndrome (PMS), for dysmenorrhea, during the menopause, for weather sensitivity (meteoropathy), for migraines, tension-type headaches, constipation, skin disorders, insomnia and dyssomnia, and during old age.

The invention also provides for the use of creatine and/or one of its claimed derivatives for the purpose of increasing muscle tissue and enhancing bodily vigor, for promoting the healing of wounds, as an agent against depression, for lowering blood pressure and for reducing body-fat.

All in all, this invention represents an important step forward in the treatment of typical disorders in women.

The following case studies serve to document the inventive achievement.

CASE STUDIES

Case 1

A 35 year-old woman (B.S). experienced complete normalization of her digestive system and bowel function after taking creatine pyruvate in doses of 3 to 8 g/d. Prior to the treatment, she had suffered for 15 years from sluggish bowels and constipation with suppressed evacuation of up to 5 days. The same dosage also effected a remarkable decrease in acne and skin uncleanness symptoms. The woman found that she was noticeably less tired in the evening, and less sleep-drunk in the morning, which she attributed to the deeper and more relaxing sleep brought about by the creatine pyruvate. Another remarkable outcome was the accelerated healing of a wound incurred through surgical correction of a fracture. This was also noticed by her doctor.

Case 2

A 30 year-old woman (A.H.) who had suffered for years from migraines provoked by heat of bodily or mental exertion was able to prevent the attacks, even under extreme conditions, by taking a daily dose of 1.5 g of creatine monohydrate. By taking creatine pyruvate, she was also able to stop the pain she had otherwise experienced during menstruation.

Case 3

A 31 year-old woman (H.H.) who had suffered for years from PMS and dysmenorrhea experienced a marked reduction in the PMS symptoms and was generally less depressed as a result of taking a daily dose of 2 to 5 g of creatine ascorbate. her otherwise very painful (dysmenorrheal) periods were almost free of pain. She also noticed the absence of skin-tissue hydropexia, with the normally attendant feeling of tautness. A positive side effect was the shrinkage of fat pads, accompanied by an increase in muscle tissue and vigor.

Case 4

A 73 year-old, postmenopausal woman (F.B.), who had suffered from depressions, lethargy and physical feebleness for 4 years, experienced a rise in spirits, became unexpectedly motivated and gained in strength on taking a daily dose of 1 to 4 g of creatine ascorbate. The improvements were also noticed by her family.

Case 5

A 38 year-old woman (J.R.) who had suffered from PMS and menstruation problems for years experienced a reduction in the PMS symptoms and a general rise in spirits on taking a daily dose of 2 to 5 g of creatine pyruvate. Her otherwise painful periods were now painless. A pronounced and sustained improvement in her emotional condition was also noticed. A positive side effect was the increase in muscle tissue and vigor, and sports activities never resulted in stiffness.

Case 6

An 80 year-old woman (F.M) who had suffered for years from depressions, lethargy and physical feebleness experienced a rise in spirits combined with unexpected new motivation and an increase in strength on taking a daily dose of 1 to 5 g of creatine monohydrate. Both she herself and her family noticed these improvements. In addition, her blood pressure—which had previously been severely hypertonic (sys up to 270)—returned to normal (BP dia70-sys130) under the influence of creatine monohydrate combined with an antihypertensive agent.

Case 7

A 25 year-old woman (M.M.), who had suffered for years from PMS, experienced complete relief of her physical complaints on taking an average daily dose of 5 g of creatine pyruvate. She no longer suffered from tenderness and swelling of the breast, or from abdominal pain, while taking the formulation.

What is claimed is:

1. A method of treating premenstrual syndrome, wherein the patient in need thereof is administered an active substance selected from the group consisting of creatine, derivatives of creatine and combination of creatine and derivatives of creatine, in a dosage which reduces or eliminates the syndrome.

2. The method of claim 1, wherein
   creatine monohydrate is administered.

3. The method of claim 1, wherein the creatine derivatives are selected from the group comprising creatine pyruvates, creatine ascorbates, creatine-α-ketoglutarates and mixtures thereof are administered.

4. The method of claim 1, wherein
   creatine and/or creatine derivatives are administered together with substances selected from the group comprising pyruvates, ascorbates, α-ketoglutarates, alkali and earth alkali salts, and mixtures thereof.

5. The method of claim 1, wherein
   the active substance is administered in daily doses of 0.1 to 20 g, especially in daily doses of 1 to 7 g.

6. The method of claim 1 as a prophylactic against premenstrual syndrome.

7. The method of claim 1 as a therapy for premenstrual syndrome.

8. The method of claim 1, wherein
   a formulation comparing said active substances is administered in the form of powders, tablets, coated tablets, pastilles, creams, pastes of in liquid form.

* * * * *